United States Patent [19]

Hallgren

[11] 4,410,464

[45] Oct. 18, 1983

[54] DIARYL CARBONATE PROCESS

[75] Inventor: John E. Hallgren, Scotia, N.Y.

[73] Assignee: General Electric Company, Schenectady, N.Y.

[21] Appl. No.: 358,493

[22] Filed: Mar. 15, 1982

[51] Int. Cl.$^3$ .............................................. C07C 68/06
[52] U.S. Cl. .................................................... 260/463
[58] Field of Search ......................................... 260/463

[56] References Cited

U.S. PATENT DOCUMENTS 4,045,464  8/1977  Romano et al. ..................... 260/463
4,201,721  5/1980  Hallgren ............................. 260/463

FOREIGN PATENT DOCUMENTS 2738437   4/1978  Fed. Rep. of Germany ...... 260/463
2736062   2/1979  Fed. Rep. of Germany ...... 260/463
2736063   2/1979  Fed. Rep. of Germany ...... 260/463
2815512  10/1979  Fed. Rep. of Germany ...... 260/463

Primary Examiner—Diana G. Rivers
Attorney, Agent, or Firm—William H. Pittman; James C. Davis, Jr.; James Magee, Jr.

[57] ABSTRACT

Diphenyl carbonates are prepared by the reaction of phenol and a dialkyl carbonate in the presence of an effective amount of a suitable catalyst and a molecular sieve. The alkyl aryl carbonate produced in the first step of the reaction can be converted to the diaryl carbonate by further reaction with phenol, in the absence of molecular sieves.

7 Claims, No Drawings

DIARYL CARBONATE PROCESS

BACKGROUND OF THE INVENTION

A number of routes for the production of polycarbonate resins are presently available, and some of these are employed commercially. Generally, the commercial processes involve the use of phosgene, but the avoidance of use of phosgene is desired, because of the toxicity of the material.

A particularly desirable route to such polycarbonate resins would involve the use of a diaryl or substituted diaryl carbonate. However, while a number of processes have been described for the production of such diaryl carbonates, none to the best of my knowledge have proven economically feasible. Frequently, such processes prove to be uneconomical because of the amount of catalyst required, the type of catalyst, reaction time and rates, or the inability to recycle the catalyst.

CROSS-REFERENCE TO RELATED APPLICATIONS

A major reactant employed in accordance with the present invention is a dialkyl carbonate. One particularly desirable method for producing such a dialkyl carbonate is described and claimed in copending application Ser. No. 319,501, filed Nov. 29, 1981, now U.S. Pat. No. 4,360,477, assigned to the same assignee as the present invention; by reference this application is made part of the disclosures of the instant application.

The present application is also related to copending application Ser. No. 338,189, filed Jan. 8, 1982, assigned to the same assignee as the present invention. In accordance with the process of that invention, diaryl and substituted diaryl carbonates are also prepared from phenols, though the other reactants according to the referenced invention are carbon monoxide and oxygen, rather than the dialkyl carbonate used in accordance with the present invention. In the referenced invention, a dialkyl carbonate is employed as an intermediate product, but it is not reacted with phenol, as in the present invention. By reference, this application is also made part of the disclosures of the instant application.

SUMMARY OF THE INVENTION

In accordance with the present invention, a process is described for the preparation of diaryl and substituted diaryl carbonates (hereinafter referred to, generically, as "diaryl carbonates") from phenol or substituted phenols (hereinafter referred to as "phenol") and a dialkyl carbonate. The reaction is carried out in the presence of a suitable catalyst and a molecular sieve. The product resulting from this initial reaction is an alkyl aryl carbonate. Diaryl carbonates can be produced, including further reaction of the alkyl aryl carbonate by methods known in the art, with phenol employed in the first step.

In accordance with the present invention, the diaryl carbonates are produced in accordance with the net reaction of equation (1):

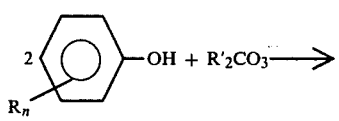

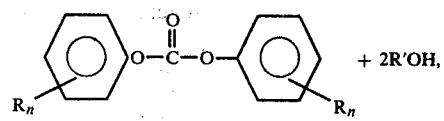

wherein R is selected from the class consisting of halogen, alkyl, alkoxy, aryl, and aryloxy groups; n is a whole number from 0 to 3; and R' is an alkyl group of $C_{1-2}$ carbon atoms, e.g., methyl, ethyl. Preferably, the reaction in accordance with the present invention is carried out in two steps, as follows:

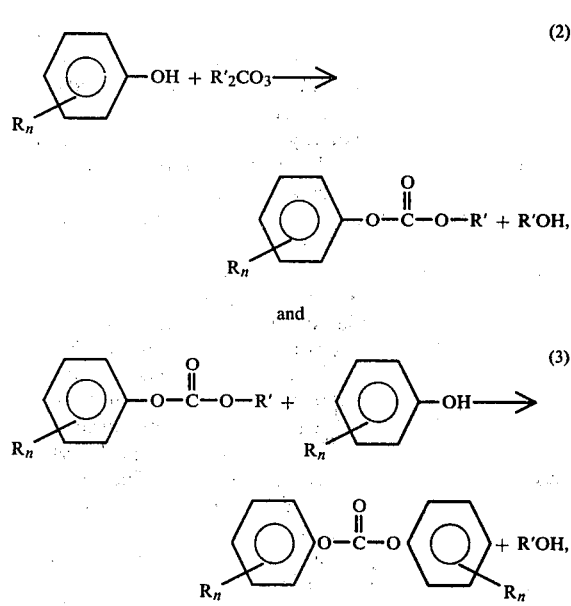

wherein R, R', and n are previously defined.

While the transesterification type of reaction is a reaction of wide industrial utility, being employed, for example, in the production of polyester resins and wire enamels, this type of reaction is reversible and is driven to completion by removal of one of the products by distillation. While in most such reactions of the prior art the equilibrium constant is near unity, the equilibrium constant for the reaction of equation (1) is not nearly so favorable, so that the reaction is much more difficult to drive to completion. While the prior art, as, for example, in Illuminati et al, U.S. Pat. No. 4,182,726, describes reactions similar to those of equation (1), the reactions are carried out in the absence of molecular sieves, thus rendering the reaction much more difficult from a standpoint of processing and yield. For example, when diphenyl carbonate is produced from phenol and dimethyl carbonate in accordance with equation (1), and in the absence of molecular sieves, a methanol-dimethyl carbonate azeotropic mixture results, and this is distilled from the reaction mixture and separated with great difficulty and requires expensive equipment.

The molecular sieves and the use of this term employed in the practice of the present invention are more particularly disclosed in U.S. Pat. Nos. 3,948,760, 4,033,858, 4,036,739, 2,882,243, 3,130,007 and 3,529,033. These sieves are generally a crystalline hydrated silica-alumina (made up predominantly, i.e., of a major proportion of $SiO_2$ and a minor proportion of aluminum oxide, $Al_2O_3$). Further examples of molecular sieves are more particularly described in a book entitled "Zeolite Molecular Sieves—Structure, Chemistry and Use", by D. W. Breck, published by John Wiley & Sons (1974). All these citations are incorporated herein by reference. These sieves have very fine pore sizes, depending upon the manner in which the sieves are made. Union Carbide Company is one of the leading manufacturers of these molecular sieves. Although the pore size of the molecular sieves can be varied within certain limits, I have found that the greatest benefits are derived when the pore size is either 4 Å or 5 Å. The larger pore sizes, such as those identified as 13X, although having some utility in the claimed process, also tend to make excessive amounts of ether compounds, such as anisole, as a result of reacting methyl phenyl carbonate and phenol. When the molecular sieves are omitted, using only the catalysts described herein, the yield of the desired diaryl carbonate is significantly reduced, so that for optimum results I have unexpectedly discovered that the simultaneous presence of this class of molecular sieves with the described catalyst greatly increases the yield of the desired product. Generally, it is desirable, as is known in the prior art, to activate the sieves by heating them in an inert atmosphere such as nitrogen at a temperature about 175° C. to 250° C. prior to their use.

The use of molecular sieves to solve the various problems suggested above has proven to be highly effective. The methanol is removed from the reaction mixture maintained at from room temperature (about 20° C.) to 200° C., and at a pressure of from atmospheric to 300 psig, allowing increased conversion to alkyl aryl carbonates in accordance with equation (2). The absorptivity and capacity of the sieves is independent of the pressure, allowing the reactions to be performed at elevated temperatures and pressures without requiring a higher concentration of methanol for efficient removal. Further, essentially pure methanol can be recovered from the molecular sieves, rather than as an azeotropic mixture with a dialkyl carbonate.

The alkyl aryl carbonate produced in accordance with equation (2) is then converted to the diaryl carbonate in accordance with the reaction of equation (3) at elevated temperatures.

Among the titanates which can be employed as catalysts in the practice of the present invention are, for instance, the alkyl and aryl type titanates of the general formula:

$$Ti(OZ)_4$$

where Z is a monovalent hydrocarbon radical, such as methyl, ethyl, propyl, butyl, hexyl, phenyl, tolyl, etc. Preferred are the aryl type titanates of the formula:

$$Ti(OAr)_4$$

where Ar is an aromatic group, such as the aforesaid phenyl, tolyl, xylyl, etc., radicals. Among such titanates may be mentioned, e.g., tetramethyl titanate, tetra-isopropyl titanate, tetraphenyl titanate, tetraoctyl titanate, tetrakis (2-ethylhexyl) titanate, tetraethyl titanate, tetracresyl titanate, tetrabutyl titanate, etc.

Among the tin salts which can be used may be mentioned, e.g., dibutyl tin diacetate, dibutyl tin oxide, dioctyl tin oxide, dihexyl tin dimethoxide, dibutyl tin dibutoxide, dibutyl tin dichloride, dioctyl tin diphenoxide, dibutyl tin diacetate, dibutyl tin dilaurate, etc. Any tin or titanate salt which can be dissolved in the reactants, namely, the dialkyl carbonates and phenol, are usually suitable for the purpose.

DESCRIPTION OF THE PREFERRED EMBODIMENTS

In accordance with the present invention, diaryl carbonates are formed from phenol and dialkyl carbonates in accordance with equation 1, the first step resulting in the production of alkyl aryl carbonates in accordance with equation 2, followed by conversion of the resulting alkyl aryl carbonate to the desired diaryl carbonate by further reaction with phenol in the presence of an effective amount of a suitable catalyst and heat. Most preferably, from the standpoint of ease of reaction and utilization of the finally prepared materials, R' is methyl and n is 0.

The production of dialkyl carbonates, particularly dimethyl carbonate, from an alkanol, carbon monoxide, and oxygen is described in a number of places. For example, a preferred method of forming the dialkyl carbonate, particularly dimethyl carbonate, is shown in the aforementioned U.S. Pat. No. 4,360,477. Other methods for forming the dialkyl carbonates are shown, for example, in the following U.S. Pat. Nos.: 3,114,762—Mador et al; 3,227,740—Fenton; 3,846,468—Pettotti et al; 3,952,045—Gaenzler; and 4,131,521—Cipris et al.

The first step of the process in accordance with the present invention, illustrated in equation (2) is carried out at a temperature of from room temperature to 200° C. at a pressure of from atmospheric to 300 psig, in the presence of a suitable titanate or tin (or mixtures thereof) catalyst and molecular sieves. Preferably, the temperature is approximately 170°–190° C. and the pressure is from 125–175 psig.

As indicated, the reaction of equation (3) is also carried out in the presence of a suitable catalyst. Catalysts found suitable for the reactions of both equations (2) and (3) include salts or alkoxides of $Al^{+3}$, $Zn^{+2}$, $Ti^{+4}$, (e.g., tetraphenoxy titanate), $Sn^{+4}$, dialkyl-tin (+4), $Zr^{+4}$, and other suitable materials. The preferred catalysts employed in accordance with the present invention are dialkyltin compounds and titanates, and the most preferred catalyst is a mixture of tetraphenyl titanate and dioctyl tin oxide dissolved in the reactants, (e.g., the dialkyl carbonate and phenol), the latter being preferably in a molar ratio of 1:1. Generally, the total amount of catalyst employed on a weight basis in the reactions of both equations (2) and (3) is from 0.01% to 2%, based on the total weight of the phenol and dialkyl carbonate. The catalyst employed in the reaction of equation (2) is preferably not removed before proceeding with the reaction of equation (3) and this constitutes a distinct advantage for my process.

The ratio of reactants in both equations (2) and (3) is preferably stoichiometric. Variations from the stoichiometry of ±25%, or even more, can readily be tolerated.

In carrying out the reaction of equation (2), molecular sieves are required in order to remove the methanol coproduced. The quantity employed can be from 8 to 20 grams or more of molecular sieve for each gram of alkanol to be absorbed as a result of the reaction of the dialkyl carbonate and phenol and preferably from 8 to 10 grams. The preferred sieves which can be employed are the 4 Å, and 5 Å sieves for the reaction as stated previously.

While the reaction can be carried out either as a batch process, or as a continuous process, from the standpoint of conversion percentages and methanol removal, the continuous process is preferred. In any event, after the alkanol is removed from the molecular sieves by heat and a stream of inert gas, such as nitrogen, the sieves are usuable for further future purposes.

The examples set forth below should not be considered as limiting, in any way, the full scope of the invention. All parts in the examples, unless otherwise indicated, are by weight.

EXAMPLE 1

A reaction apparatus was constructed by connecting two stainless steel tubes with a piece of 1/16 inch tubing. The stainless steel tubes were 2 feet long, with an outside diameter of ⅜ inch and an inside diameter of approximately ¼ inch, and the tubes were wrapped with heating tape. The tubes were then filled with Linde 5 Å molecular sieves in an amount of 37.4 parts. A reciprocating pump, capable of withstanding 3,000 psig, and a back pressure regulator to control pressures in the columns, were connected to the reaction apparatus. A mixture of 90 parts dimethyl carbonate and 94 parts phenol, in the presence of 1.076% dioctyl tin oxide and 0.55%, by weight, based on the weight of the reactants of tetraisopropyl titanate, was pumped through the bed of the molecular sieves maintained at a temperature of 180±5° C. and at a pressure of 200 psig at a flow rate of 1.0±0.1 ml/min. Phenyl methyl carbonate, at a conversion rate of approximately 20% based upon the dimethyl carbonate, was produced, along with methanol. The methanol was absorbed by the molecular sieves which were then regenerated in a stream of nitrogen at 250° C. for 2 hours. The methanol could be recovered and the molecular sieves were reused.

EXAMPLE 2

The mixture from Example 1 containing the phenyl methyl carbonate, unreacted phenol, and dimethyl carbonate, along with dioctyl tin oxide and tetraisopropyl titanate catalysts in the absence of molecular sieves was heated to 100° C. to remove the dimethyl carbonate. After heating at 185°–195° C. for 2 hours an 82% conversion of methyl phenyl carbonate to diphenyl carbonate resulted as illustrated in equation (3).

EXAMPLE 3

A reaction equivalent to Example 1 was carried out employing Linde 4 Å molecular sieves in place of the Linde 5 Å molecular sieves, with equivalent results.

EXAMPLE 4

A reaction equivalent to that of Example 1 was carried out employing Linde 13X molecular sieves in place of the Linde 5 Å molecular sieves. Although some methyl phenyl carbonate was obtained, large quantities of anisole were generated thus negating the objective of the invention.

EXAMPLE 5

A reaction equivalent to Example 1 was carried out, but employing Linde 3 Å molecular sieves, in place of the Linde 5 Å sieves. Very poor conversion to phenyl methyl carbonate was obtained.

EXAMPLE 6

To illustrate the requirement for employing both a suitable catalyst and the specific molecular sieves, in accordance with the present invention, a series of runs were made in a static apparatus rather than on a continuous basis at 180° C. under autogeneous pressure. The catalyst employed was dioctyl tin oxide in an amount of approximately 0.05%, by weight of the phenol and dimethyl carbonate, and the molecular sieve was Linde 5 Å in an amount of approximately 1 part for each 2 parts of reactants, the results obtained were as follows:

| Catalyst | Molecular Sieves | Percent Conversion |
| --- | --- | --- |
| None | Present | 0 |
| Present | None | Less than 1 |
| Present | Present | 6.5 |

EXAMPLE 7

An apparatus of the type described in Example 1 was employed, the stainless steel tubes being packed with a total of 31.8 parts of Linde 5 Å molecular sieves which had been activated in a nitrogen stream at 200° C. A quantity of 188 parts of phenol, 180 parts of dimethyl carbonate, and 1 part dioctyl tin oxide was warmed to 80° C. to effect solution of the catalyst and was then pumped at a rate of 0.8 ml/min through the columns which were maintained at 180° C. with a pressure of 150 psig. A quantity of 132 parts of effluent was collected and analyzed by vapor phase chromotography to show a 9.1% conversion of the phenol to phenyl methyl carbonate. A quantity of 9.4 parts of methanol was absorbed for each 100 parts of sieves present. The columns of molecular sieves were regenerated by heating to 220° C. in in a stream of nitrogen with recovery of the methanol.

EXAMPLE 8

A quantity of 15.2 parts of phenyl methyl carbonate, 9.4 parts of phenol, and 1.0 part of dioctyl tin oxide was heated in a reaction vessel to 190°–210° C. for 1 hour. Methanol was distilled from the reaction mixture. Analysis of the pot residue indicated an 80% conversion to diphenyl carbonate.

Results equivalent to those of Example 1 may be obtained employing diethyl carbonate in place of dimethyl carbonate. Similarly, results equivalent to those of Example 1 may be obtained employing phenols substituted as indicated by the definition of R, in place of unsubstituted phenol.

While specific examples of the invention have been shown and described, the invention should be considered as limited only by the appended claims.

What I claim as new and desire to secure by Letters Patent of the United States is:

1. A process for the production of diaryl carbonates comprising:
   A. producing an aryl alkyl carbonate by reacting a dialkyl carbonate with a phenol in accordance with the equation:

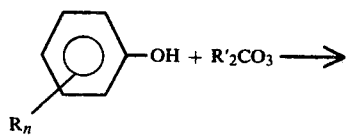

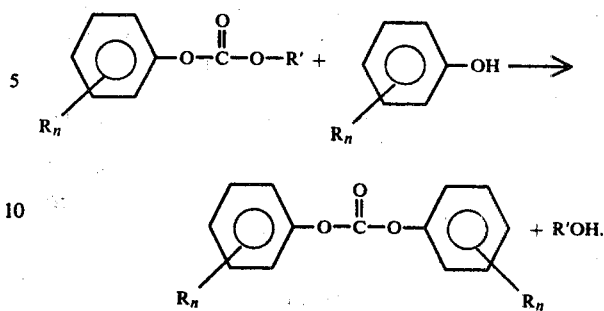

wherein R is selected from the class consisting of halogen, alkyl, alkoxy, aryl and aryloxy groups; n is a whole number from 0 to 3; and R' is methyl or ethyl, in the presence of an effective amount of a catalyst comprising a salt or alkoxide of $Al^{+3}$, $Zn^{+2}$, $Ti^{+4}$, $Sn^{+4}$ or $Zr^{+4}$ and a methanol- or ethanol-removing amount of a crystalline hydrated silica-alumina molecular sieve having a pore size from 4 Å to 5 Å, said methanol- or ethanol-removing amount being about 8 to 20 parts per part of methanol or ethanol liberated, and B. reacting said aryl alkyl carbonate with an additional amount of said phenol at an elevated temperature in the presence of a catalyst, to produce the diaryl carbonate in accordance with the equation:

2. The process of claim 1 wherein R' is methyl and n is 0.

3. The process of claim 1 wherein the reaction between the dialkyl carbonate and the phenol is carried out at from room temperature to 200° C.

4. The process of claim 1 wherein the pressure employed in the reaction between the diaryl carbonate and phenol is from atmospheric to 300 psig.

5. The process of claim 1 wherein the catalyst employed is a titanate ester.

6. The process of claim 1 wherein the catalyst employed is a tin catalyst.

7. The process of claim 1 wherein the catalyst employed is a mixture of a titanate ester and a tin catalyst.

* * * * *